(12) United States Patent
Hugo et al.

(10) Patent No.: US 7,323,598 B2
(45) Date of Patent: *Jan. 29, 2008

(54) PREPARATION OF XYLYLENEDIAMINE (XDA)

(75) Inventors: Randolf Hugo, Dirmstein (DE); Sabine Jourdan, Mannheim (DE); Kirsten Wenz, Mannheim (DE); Thomas Preiss, Weisenheim Am Sand (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 48 days.

This patent is subject to a terminal disclaimer.

(21) Appl. No.: 10/571,615

(22) PCT Filed: Sep. 4, 2004

(86) PCT No.: PCT/EP2004/009883

§ 371 (c)(1),
(2), (4) Date: Mar. 10, 2006

(87) PCT Pub. No.: WO2005/026102

PCT Pub. Date: Mar. 24, 2005

(65) Prior Publication Data

US 2007/0088178 A1 Apr. 19, 2007

(30) Foreign Application Priority Data

Sep. 10, 2003 (DE) ................................ 103 41 612

(51) Int. Cl.
*C07C 209/00* (2006.01)
(52) U.S. Cl. ..................................................... 564/415
(58) Field of Classification Search ...................... None
See application file for complete search history.

(56) References Cited

U.S. PATENT DOCUMENTS

| 2002/0038054 A1 | 3/2002 | Hurley et al. |
| 2003/0013917 A1 | 1/2003 | Nakamura et al. |

FOREIGN PATENT DOCUMENTS

| DE | 2041360 | 2/1971 |
| EP | 1193244 | 4/2002 |
| EP | 1279661 | 1/2003 |
| GB | 1306449 | 2/1973 |
| WO | WO-2005028417 | 3/2005 |

*Primary Examiner*—Samuel Barts
(74) *Attorney, Agent, or Firm*—Connolly Bove Lodge & Hutz LLP

(57) ABSTRACT

A process for preparing xylylenediamine, comprising the steps of ammoxidizing xylene to phthalonitrile by contacting the vaporous product of this ammoxidation stage directly with a liquid organic solvent (quench), removing products having a boiling point higher than phthalonitrile (high boilers) from the resulting quench solution or suspension and hydrogenating the phthalonitrile, wherein the organic solvent used for the quench is N-methyl-2-pyrrolidone (NMP), after the removal of the high boilers and before the hydrogenation, there is a partial or complete removal of the NMP and/or of products having a boiling point lower than phthalonitrile (low boilers) and the phthalonitrile for the hydrogenation step is dissolved or suspended in an organic solvent or in liquid ammon.

19 Claims, 1 Drawing Sheet

PREPARATION OF XYLYLENEDIAMINE (XDA)

CROSS REFERENCE TO RELATED APPLICATION

The present application is a National Stage application of PCT/EP2004/009883, filed Sep. 4, 2004, which claims priority from German Patent Application No. 103 41 612.9, filed Sep. 10, 2003.

BACKGROUND

The present invention relates to a process for preparing xylylenediamine, comprising the steps of ammoxidizing xylene to phthalonitrile, by contacting the vaporous product of this ammoxidation stage directly with a liquid organic solvent (quench), removing products having a boiling point higher than phthalonitrile (high boilers) from the resulting quench solution or suspension and hydrogenating the phthalonitrile, Xylylenediamine(bis(aminomethyl)benzene) is a useful starting material, for example for the synthesis of polyamides, epoxy hardeners or as an intermediate for preparing isocyanates.

The term "xylylenediamine" (XDA) includes the three isomers ortho-xylylenediamine, meta-xylylenediamine (MXDA) and para-xylylenediamine.

The term "phthalonitrile" (PN) includes the three isomers, 1,2-dicyanobenzene=o-phthalonitrile, 1,3-dicyanobenzene=isophthalonitrile=IPN and 1,4-dicyanobenzene=terephthalonitrile.

The two-stage synthesis of xylylenediamine by ammoxidizing xylene and subsequently hydrogenating the resulting phthalonitrile is known.

EP-A2-1 113 001 (Mitsubishi Gas Chem. Comp.) describes a process for preparing nitrile compounds by ammoxidizing corresponding carbocyclic or heterocyclic compounds, in which excess ammonia from the reaction product is recycled. Also described is the direct contacting of the vaporous product of the ammoxidation stage with a liquid organic solvent which is in particular aliphatic or aromatic hydrocarbons (paragraphs [0045] and [0046]).

EP-A2-1 193 247 and EP-A1-1 279 661 (both Mitsubishi Gas Chem. Comp.) relate to a process for purifying isophthalonitrile (IPN) and to a process for preparing pure XDA respectively, in which the phthalonitrile is synthesized by ammoxidizing xylene, and the vaporous product of the ammoxidation stage is contacted directly with a liquid organic solvent (quench). The organic solvent is selected from alkylbenzenes, heterocyclic compounds, aromatic nitriles and heterocyclic nitriles, and has a boiling point which is below that of phthalonitrile (EP-A2-1 193 247: column 4, paragraph [0018] and [0019]; EP-A1-1 279 661: columns 4-5, paragraph [0023] and [0024]).

EP-A2-1 193 244 (Mitsubishi Gas Chem. Comp.) describes a process for preparing XDA by hydrogenating phthalonitrile which is synthesized in a preceding stage by ammoxidizing xylene, in which the vaporous product of the ammoxidation stage is contacted directly with a liquid organic solvent (quench) and the resulting quench solution or suspension is fed to the hydrogenation.

Preferred organic solvents are $C_6$-$C_{12}$ aromatic hydrocarbons such as xylene and pseudocumene (column 6, paragraph [0027] and [0028]).

DE-A-21 64 169 describes, on page 6, last paragraph, the hydrogenation of IPN to meta-XDA in the presence of an Ni and/or Co catalyst in ammonia as a solvent.

Five parallel BASF patent applications each having the same application date each relate to processes for preparing XDA.

BRIEF SUMMARY

It is an object of the present invention to provide an improved, economically viable process for preparing highly pure xylylenediamine, in particular meta-xylylenediamine, with high yield and space-time yield (STY), which, at comparable throughputs to known processes, for example the process according to EP-A2-1 193 244, enables smaller apparatus and machines as a consequence of reduced streams, in particular solvent streams, including recycle streams.

We have found that this object is achieved by a process for preparing xylylenediamine, comprising the steps of ammoxidizing xylene to phthalonitrile by contacting the vaporous product of this ammoxidation stage directly with a liquid organic solvent (quench), removing products having a boiling point higher than phthalonitrile (high boilers) from the resulting quench solution or suspension and hydrogenating the phthalonitrile, wherein the organic solvent used for the quench is N-methyl-2-pyrrolidone (NMP), after the removal of the high boilers and before the hydrogenation, there is a partial or complete removal of the NMP and/or products having a boiling point lower than phthalonitrile (low boilers) and the phthalonitrile for the hydrogenation step is dissolved or suspended in an organic solvent or in liquid ammonia.

The process according to the invention preferably finds use for preparing meta-xylylenediamine (MXDA) by hydrogenating isophthalonitrile (IPN) which is synthesized in a preceding stage by ammoxidizing meta-xylene.

DETAILED DESCRIPTION OF THE DISCLOSURE

Figure 1:
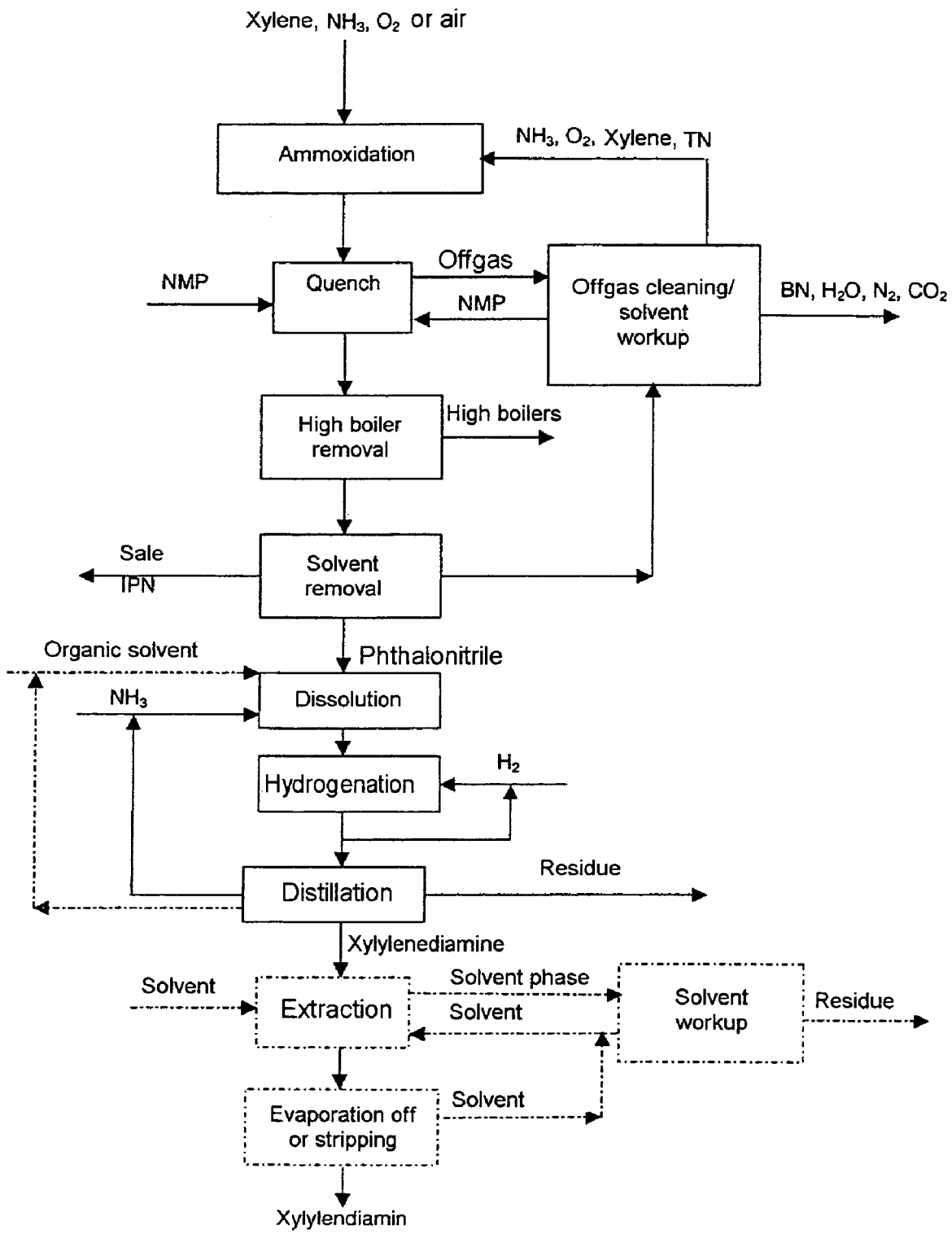
FIG. 1 shows a schematic illustration of a process for preparing xylylenediamine according to the present invention.

The process according to the invention can be performed as follows:

Ammoxidation stage:

The ammoxidation of xylene (o-, m- or p-xylene) to the corresponding phthalonitrile (ortho-xylene→o-phthalonitrile; meta-xylene→isophthalonitrile; para-xylene→terephthalonitrile) is generally carried out by processes known to those skilled in the art.

The ammoxidation of methyl aromatics is preferably carried out over a multioxide catalyst with ammonia and an oxygenous gas (oxygen or air or both) in a fluidized bed reactor or a tube (bundle) reactor.

The reaction temperature is generally from 300 to 500° C., preferably from 330 to 480° C.

The catalyst preferably contains V, Sb and/or Cr and is more preferably composed of [V, Sb and alkali metals] or [V, Cr, Mo and B], in each case as an unsupported catalyst or on an inert support.

Preferred inert supports are $SiO_2$, $Al_2O_3$ or a mixture of both, or steatite.

Such a procedure is described, for example, in the BASF patent applications EP-A-767 165 and EP-A-699 476, which are explicitly incorporated herein by way of reference.

The BASF patent applications EP-A-222 249, DE-A-35 40 517 and DE-A-37 00 710 also disclose suitable ammoxidation catalysts.

The ammoxidation may also be carried out in accordance with the processes described in the applications cited at the outset, EP-A2-1 113 001, EP-A2-1 193 247, EP-A1-1 279 661 and EP-A2-1 193 244.

Quench:

The vapor produced in the ammoxidation, comprising the product of value, phthalonitrile, is contacted directly with the liquid organic solvent N-methyl-2-pyrrolidone (quench with NMP as a quench liquid, quenching agent).

The NMP used for the quench may already contain dissolved or suspended phthalonitrile (preferably that isomer which corresponds to the synthesized PN).

The sudden temperature reduction when contacting the vaporous phthalonitrile with the liquid solvent NMP (quench) reduces the formation of undesired secondary and decomposition products which lead to a reduction in the quality of the phthalonitrile and finally of the XDA.

The vaporous phthalonitrile is absorbed by the quench directly into the liquid NMP solvent resulting in a solution and/or a suspension which can be directly processed further.

The fresh feed used is generally technical-grade NMP having a purity of >99% by weight, in particular >99.5% by weight.

Preference is given to using NMP recovered from the process as quench liquid. The purity here of the quench liquid may also be $\leq$99% by weight, for example 90-98% by weight, especially when the impurities are substances which are not foreign to the process (i.e., inter alia, water, ammonia, benzonitrile, tolunitrile, xylene, o-, m- or p-methylbenzylamine, benzylamine, xylylenediamine).

The amount of the solvent NMP used is generally such that solutions/suspensions are obtained which have a phthalonitrile content of from 15 to 75% by weight, preferably from 25 to 60% by weight.

The vaporous effluent of the ammoxidation, comprising the phthalonitrile (PN), is introduced into the liquid in a quench apparatus, for example preferably in a falling-film condenser (thin-film, trickle-film or falling-stream condenser), in a jet apparatus or in a column. In this apparatus, the vaporous phthalonitrile may be conducted in cocurrent or in countercurrent with the liquid solvent. In the case of cocurrent flow, the vaporous phthalonitrile is introduced into the quench apparatus from above. It is advantageous to feed the liquid solvent tangentially at the top of the falling-film condenser or to feed the liquid solvent through one or more nozzles, in order to achieve complete wetting of the interior wall of the quench apparatus.

In the case of a quench column, the gas from the ammoxidation is introduced at the bottom of the column and the solvent is fed at the top. To increase the surface area available for condensation, the quench apparatus may be equipped with internals such as trays, structured packings or random packings.

The NMP for the quench may be used in single pass or as circulation liquid.

Advantageously, a portion of the quench solution or suspension is recycled.

A heat transferor installed in the circuit is used to cool the quench solution or suspension.

The temperature of the circulation medium and the circuit flow rate are set and adjusted with respect to each other in such a way that the desired temperature in the quench exit is achieved. The smaller the flow rate of the circulation medium, the lower the temperature selected of the circulation medium and vice versa, although solubilities and melting points, and also the hydraulic stress limits of the quench apparatus, have to be taken into account.

The flow rate of the freshly fed NMP is dependent upon the quench temperature. It is set in such a way that the desired concentration of the PN solution or suspension is obtained. Since the solubility of PN in NMP rises with increasing temperature, a higher PN concentration in the NMP can be conveyed with increasing quench exit temperature.

The circulation medium is fed in together with the fresh solvent or separately, at a suitable point in the quench apparatus.

In the case of a quench column operated in countercurrent, the fresh NMP is fed at the top and the circulation medium further down, in about the middle of the column.

In general, heating of the NMP and/or of the circulation medium used sets the temperature of the liquid quench effluent to from 40 to 180° C., preferably from 50 to 120° C., in particular from 80 to 120° C.

The boiling point of phthalonitrile in the range from 1 to 100 mbar is approx. 60 Kelvin above the boiling point of NMP.

The absolute pressure in the course of quenching is generally from 0.5 to 1.5 bar. Preference is given to operating at slightly elevated pressure.

Xylene, water, $NH_3$, $CO_2$, $N_2$, etc., which are generally present in the vaporous effluent of the ammoxidation are only partly or virtually not dissolved under the quench conditions in the quench NMP solvent and are removed from the quench apparatus in predominantly gaseous form.

Removal of products having a boiling point higher than phthalonitrile (at the same pressure) (high boilers) from the resulting quench solution or suspension:

High boilers are preferably removed by distillation from the quench solution or suspension obtained.

The high boilers may be removed from the resulting quench solution or suspension in one or more evaporator stages connected in series or in a distillation column, in which case the high boilers are discharged via the bottom, while phthalonitrile together with the NMP solvent and low boilers are removed via the top.

Preference is given to using a distillation column for high boiler removal.

The column is preferably equipped with the customary internals for increasing the separating performance such as trays, structured or random packings, etc.

The configuration of the column (in particular number of separating stages, feed point, reflux ratio, etc.) may, adapted to the particular composition of the solution, be carried out by those skilled in the art by methods familiar to them. Preference is given to operating under reduced pressure, in order to limit the bottom temperature.

Partial or complete removal of the NMP and/or of products having a boiling point lower than phthalonitrile (at the same pressure) (low boilers):

The lower the temperature in the quench step, the higher the proportion of water and secondary components which have a lower boiling point than PN (at the same pressure) (for example benzonitrile, tolunitrile) in the liquid quench effluent.

In the process according to the invention, before the hydrogenation of the phthalonitrile, water and products having a boiling point lower than phthalonitrile (at the same pressure) (low boilers; for example, unconverted xylene, benzonitrile, tolunitrile, each as a heteroazeotrope with water, water, benzonitrile, tolunitrile; listing with increasing boiling point (at the same pressure); and in some cases also, benzylamine, o-, m-, p-methylbenzylamine, xylylenediamines, in which case these amines stem from recycled solvent from the hydrogenation stage) are partly or fully removed from the resulting quench solution or suspension after the high boiler removal. This removal is preferably by distillation.

The NMP used in the quench as a low boiler can be partly or completely removed in this step.

This removal of the NMP and/or of the low boilers may be effected in one or more evaporator stages connected in series or in a distillation column via the top.

Preference is given to using a distillation column which is equipped preferably with the customary internals for increasing the separating performance, such as trays, structured or random packings, etc.

The configuration of the column (in particular number of separating stages, feed point, reflux ratio, etc.), adapted to the particular composition of the solution or suspension, may be carried out by those skilled in the art by methods familiar to them.

Preference is given to operating under reduced pressure, in order to limit the bottom temperature.

Combination of the low boiler and high boiler removal in a sidestream column, in particular dividing wall column with sidestream:

The removal of high boilers from the resulting quench solution or suspension via the bottom and the removal of the NMP and/or low boilers via the top is more preferably effected in a single column which is configured as a sidestream column.

The phthalonitrile is withdrawn in liquid form from a sidestream in the rectifying section or in vapor form from a sidestream in the stripping section of the column.

The configuration of the column (in particular number of separating stages, feed point, reflux ratio, location of the sidestream, etc.) may, adapted to the particular composition of the solution, be carried out by those skilled in the art by methods familiar to them.

Preference is given to operating under reduced pressure (for example from 30 to 250 mbar (abs.), in particular from 50 to 100 mbar (abs.)), in order to limit the bottom temperature.

In a further particular process embodiment, the high boilers are removed from the resulting quench solution or suspension via the bottom and the NMP and/or low boilers are removed via the top in a single column which is configured as a dividing wall column with a sidestream.

The phthalonitrile is withdrawn in liquid form from a sidestream in the region of the dividing wall.

Suitable dividing wall columns are known to those skilled in the art, for example, from Hydrocarbon Processing, March 2002, page 50 B-50 D; EP-A-1 040 857, DE-A1-101 00 552, WO-A-02/40434, U.S. Pat. No. 4,230,533, EP-A1-638 778, EP-A1-1 181 964, WO-A-02/45811, EP-A1-1 205 460, DE-A1-198 13 720, EP-A1-1 084 741.

Hydrogenation:

For the hydrogenation of the phthalonitrile to the corresponding xylylenediamine (o-, m- or p-xylylenediamine), the PN obtained in the above steps is optionally dissolved or suspended in an organic solvent or in liquid ammonia.

Preferred solvents are NMP, xylene, benzylamine, o-, m- or p-methylbenzylamine, xylylenediamine and mixtures thereof. When the NMP has only partly been removed, if at all, in the step of NMP and/or low boiler removal, the resulting solution or suspension of PN in NMP may be conducted into the hydrogenation.

For the hydrogenation of the phthalonitriles to the xylylenediamine, the solution or suspension is added, preferably in liquid form, in an organic solvent, more preferably ammonia. The ammonia may be added directly after the stage of the NMP and/or low boiler removal or not until the hydrogenation stage.

In this case, the weight ratio in the fresh feed of dinitrile to ammonia is generally from 1:0.15 to 1:15, preferably from 1:0.5 to 1:10, more preferably from 1:1 to 1:5.

For the hydrogenation, the catalysts and reactors (for example fixed bed or suspension method), and also processes (continuous, semicontinuous, batchwise), which are known to those skilled in the art for this reaction may be employed.

In the fixed bed catalyst method, both the liquid phase and the trickle method are possible. Preference is given to a trickle method.

In this regard, reference is made, for example, to the processes described in the applications GB-A-852,972 (equivalent: DE-A-11 19 285) (BASF AG) and DE-A-12 59 899 (BASF AG) and to the U.S. Pat. No. 3,069,469 (California Research Corp.).

The hydrogenation reactor may be operated in straight pass. Alternatively, a circulation method is also possible, in which a portion of the reactor effluent is recycled to the reactor inlet, preferably without preceding workup of the circulation stream. This allows optimum dilution of the reaction solution to be achieved, which has a favorable effect on the selectivity. In particular, the circulation stream may be cooled in a simple and inexpensive manner by means of an external heat transferor, and the heat of reaction thus removed. The reactor can also be operated adiabatically, in which case the temperature rise of the reaction solution may be limited by the cooled circulation stream. Since the reactor itself then does not have to be cooled, a simple and inexpensive design is possible. An alternative is a cooled tube bundle reactor.

Preference is given to catalysts which contain cobalt and/or nickel and/or iron, as an unsupported catalyst or on an inert support.

The reaction temperatures are generally from 40 to 150° C., preferably from 40 to 120° C.

The pressure is generally from 40 to 300 bar, preferably from 100 to 200 bar.

Isolation of the XDA:

After the hydrogenation any solvent used and any ammonia used are distilled off.

Preference is given to purifying the xylylenediamine by distilling off relatively low-boiling by-products (at the same pressure) via the top and removing relatively high-boiling impurities via the bottom by distillation.

Particular preference is given to the method in which, after the hydrogenation, the solvent, any ammonia and also any relatively low-boiling by-products are distilled off via the top and, afterwards, relatively high-boiling impurities are removed from the xylylenediamine by distillation via the bottom.

In a particular embodiment, the removal of relatively low-boiling and relatively high-boiling by-products may also be effected in a sidestream or dividing wall column, in which case pure xylylenediamine may be obtained via a liquid or gaseous sidestream.

Depending on the desired purity, the product (XDA) is additionally extracted with an organic solvent, preferably an aliphatic hydrocarbon, in particular a cycloaliphatic hydrocarbon, very particularly cyclohexane or methylcyclohexane.

This purification by extraction may be effected, for example, according to DE-A-1 074 592.

A schematic overview of a preferred embodiment of the process according to the invention is given by FIG. 1 in the appendix.

The optional process steps for solvent circulation in the hydrogenation and for 'extractive XDA purification' are indicated by dashed lines.

EXAMPLES

Example 1

Ammoxidation of m-xylene, subsequent quenching of the reaction gases with NMP as a solvent and hydrogenation of the IPN formed in the ammoxidation stage (cf. process scheme in FIG. 1)

A catalyst having the composition $V_4Sb_3W_{0.4}Cs_{0.2}$ on steatite was installed into a tubular reactor as a fixed bed. The apparatus was heated externally to 400° C. Evaporated m-xylene, gaseous ammonia, air and nitrogen were introduced to the reactor ($NH_3$/m-xylene=8 mol/1 mol; $O_2$/m-xylene=4 mol/1 mol). The furthest upstream part of the reactor was filled with an inert bed, so that the starting materials reached the reaction zone premixed and preheated to 400° C. In the reactor there was a slightly elevated pressure of 0.02-0.03 bar. The hotspot temperature reached 450° C. After conversion (C) of m-xylene of 79%, a selectivity (S) for IPN of 68% was achieved.

The gas mixture leaving the reactor is quenched in a column with NMP. A solution of IPN in NMP is discharged from the quench column at 120° C. and contains 0.6% by weight of m-xylene, 1.7% by weight of water, 0.1% by weight of benzonitrile, 3.4% by weight of tolunitrile, 19% by weight of IPN and approx. 75% by weight of NMP. Unconverted reaction gases and inert gases, and also unconverted m-xylene and a little NMP, are withdrawn in gaseous form via the top of the quench column. This gas may be worked up, in order to recycle the materials of value (in particular $NH_3$, m-xylene, NMP and tolunitrile) into the reaction stage or into the quench circuit. Inerts and secondary components ($H_2O$, benzonitrile, $N_2$, $CO_2$, etc.) are discharged from the workup stage.

The solution of IPN in NMP, obtained after the quench, is conducted at 70 mbar (abs.) to the top of a stripping column in which high-boiling secondary components are removed via the bottom. NMP, IPN and the low-boiling secondary components still present (xylene, tolunitrile, benzonitrile, etc.) are removed via the top. The bottom temperature of the column is 200° C., the top temperature 140° C. The top takeoff stream is conducted directly, i.e. without condensation, to one of the middle stages of a second column which is likewise operated at 70 mbar (abs.). IPN is removed in a purity of more than 99.9% via the bottom, while solvent and secondary components are removed via the top. The bottom temperature of this column is 185° C.

A mixture consisting of 15% by weight of IPN and 85% by weight of MXDA which had been mixed together from the pure components was hydrogenated over an unsupported cobalt catalyst at 60° C. and 190 bar in a continuous 70 ml stirred reactor. Every hour, 117 g of IPN solution and also 150 g of ammonia were passed over the catalyst. A quarter of the volume flow rate was recycled as solvent. The yield of MXDA was 92% based on IPN used.

In subsequent distillation steps, first ammonia at 190° C. and the low- and high-boiling impurities were removed in a batch distillation at a top pressure of 57 mbar and a bottom temperature of approx. 180° C. MXDA was obtained in a purity of more than 99.9% by weight.

(The data of the quench step and the distillations reported above are the results of a thermodynamic simulation. In this simulation, the quench was considered to be an apparatus in which there is thermodynamic equilibrium between gas and liquid phase. In addition to the pure material data of the components involved, real binary data were used in the calculation. Such calculations can be carried out with commercial calculation programs, here: Aspen Plus, which are familiar to those skilled in the art.)

Example 2

Alternative Hydrogenation Conditions

A mixture consisting of 27% by weight of IPN and 73% by weight of NMP which had been mixed together from the pure components was hydrogenated over an unsupported cobalt catalyst at 80° C. and 190 bar in a continuous 70 ml stirred reactor. Every hour, 70 g of IPN solution and also 90 g of ammonia were passed over the catalyst. The yield of MXDA was 96% based on IPN used.

In subsequent distillation steps, first ammonia and then NMP and low-boiling secondary components are removed. After the high-boiling purities had been removed, MXDA is obtained in a purity of more than 99.9% by weight.

Example 3

Alternative Hydrogenation Conditions

A mixture consisting of 27% by weight of IPN and 73% by weight of NMP which had been mixed together from the pure components was hydrogenated over an unsupported cobalt catalyst at 80° C. and 190 bar in a continuous 70 ml stirred reactor. Every hour, 70 g of IPN solution and also 54 g of ammonia were passed over the catalyst. The same volume flow rate is recycled as solvent. The yield of MXDA was 95.5% based on IPN used.

Example 4

Alternative Hydrogenation Conditions

A mixture consisting of 15% by weight of IPN and 85% by weight of NMP which had been mixed together from the pure components was hydrogenated over an unsupported cobalt catalyst at 80° C. and 190 bar in a continuous 70 ml stirred reactor. Every hour, 140 g of IPN solution and also 72 g of ammonia were passed over the catalyst. The yield of MXDA was 96% based on IPN used.

Example 5

Alternative Hydrogenation Conditions 30 g of IPN and 5 g of Raney nickel were initially charged in a stirred autoclave. After 66 g of ammonia had been added, 50 bar of hydrogen were injected and the autoclave was heated to 100° C. Injection of further hydrogen maintained an overall pressure of 100 bar for 5 hours. The conversion of IPN was quantitative, and a yield of 94% based on IPN used was obtained.

Example 6

The ammoxidation, the quenching and the high boiler removal were carried out as described in example 1. However, the procedure for the solvent removal is that IPN in NMP is removed (35% by weight of IPN, 62% by weight of NMP, approx. 3% of tolunitrile) via the bottom at 126° C. The remainder of the solvent and the low-boiling secondary components are removed via the top.

(The solvent removal is the result of a thermodynamic simulation as described above).

Example 7

Investigations of Solubility of IPN in Different Solvents

The solubility of IPN in NMP is approx. 26% by weight at 60° C. and approx. 41% by weight at 90° C.

At 90° C., pseudocumene attains a solubility of only 20% by weight and mesitylene of only 12% by weight.

At 60° C., the solubility of IPN in mesitylene or pseudocumene is in each case below 10% by weight.

Example 8

Ammoxidation of m-xylene, Subsequent Quenching of the Reaction Gases Using NMP as a Solvent A catalyst of the composition $V_4Sb_3K_{0.4}Ba_{0.2}$ on steatite was installed in a tubular reactor as a fixed bed. The apparatus was heated to 415° C. externally. To the reactor were fed evaporated m-xylene, gaseous ammonia and air ($NH_3$/m-xylene=14 mol/1 mol; $O_2$/m-xylene=4 mol/1 mol). The catalyst of the first half of the reactor was diluted with 70% by weight of steatite spheres, the second half with 40% by weight. In the reactor, there was a slightly elevated pressure of 0.02 bar. The hotspot temperature reached 430° C. At a conversion of m-xylene of 88% by weight, a selectivity for IPN of 71% was obtained.

The gas mixture leaving the reactor is quenched with NMP in a column. From the quench column, a solution of IPN in NMP is discharged at 120° C. and 1.02 bar (abs.) and contains 0.25% by weight of m-xylene, 1.3% by weight of water, 3.6% by weight of tolunitrile, 27% by weight of IPN and approx. 67.7% by weight of NMP. Unconverted reaction gases and inert gases, and also unconverted m-xylene and a little NMP, are removed in gaseous form via the top of the quench column. This gas may be worked up in order to recycle the materials of value (in particular $NH_3$, m-xylene, NMP and tolunitrile) into the reaction stage or into the quench circuit. Inerts and accompanying components ($H_2O$, $N_2$, $CO_2$, etc.) are discharged from the workup stage.

(The above-reported data of the quench step are the results of a thermodynamic simulation, carried out as in example 1).

Example 9

A solution corresponding to the calculated composition at the quench outlet, consisting of 0.44 g of m-xylene, 1.7 g of water, 0.88 g of benzonitrile, 3.1 g of tolunitrile, 24 g of IPN and 58 g of NMP, was mixed together from the pure components and fed to the hydrogenation. For the hydrogenation, liquid $NH_3$ was metered into the mixture ($NH_3$/IPN=14 mol/1 mol). The hydrogenation was effected in the presence of $H_2$ and 5 g of Raney nickel catalyst at 100° C. and a pressure of 100 bar in a stirred autoclave. The conversion of IPN was quantitative, and a yield of MXDA of 92% based on IPN used was obtained.

We claim:

1. A process for preparing meta- or para-xylylenediamine, comprising the steps of ammoxidizing meta- or para-xylene to iso- or terephthalonitrile, by contacting the vaporous product of this ammoxidation stage directly with a liquid organic solvent (quench),
   removing products having a boiling point higher than phthalonitrile (high boilers) from the resulting quench solution or suspension and hydrogenating the phthalonitrile,
   wherein the organic solvent used for the quench is N-methyl-2-pyrrolidone (NMP), after the removal of the high boilers and before the hydrogenation, there is a partial or complete removal of the NMP and/or of products having a boiling point lower than phthalonitrile (low boilers) and
   the phthalonitrile for the hydrogenation step is dissolved or suspended in an organic solvent or in liquid ammonia.

2. The process according to claim 1, wherein the high boilers are removed distillatively from the resulting quench solution or suspension via the bottom, while phthalonitrile is removed via the top together with the NMP solvent and low boilers.

3. The process according to claim 1, wherein, after the removal of the high boilers, the NMP is removed partly or completely and/or low boilers are removed distillatively via the top.

4. The process according to claim 1, wherein the resulting quench solution or suspension is separated into high boilers, low boilers and NMP phthalonitrile in a sidestream column in such a way that high boilers are removed via the bottom, NMP and/or low boilers via the top and phthalonitrile via a sidestream.

5. The process according to claim 1, wherein the resulting quench solution or suspension is separated into high boilers, low boilers and NMP and phthalonitrile in a dividing wall column in such a way that high boilers are removed via the bottom, NMP and/or low boilers via the top and phthalonitrile via a sidestream in the dividing wall region of the column.

6. The process according to claim 1, wherein the phthalonitrile for the hydrogenation step is dissolved or suspended in NMP, xylene, benzylamine, tolylamine and/or xylylenediamine.

7. The process according to claim 1, wherein the hydrogenation is carried out in the presence of ammonia.

8. The process according to claim 1, wherein the ammoxidation is carried out at temperatures of from 300 to 500° C. over a catalyst containing V, Sb and/or Cr, as an unsupported catalyst or on an inert support.

9. The process according to claim 1, wherein the temperature of the quench effluent in the quench with NMP is from 40 to 180° C.

10. The process according to claim 1, wherein the hydrogenation is carried out at temperatures of from 40 to 150° C. over a catalyst containing Ni, Co and/or Fe, as an unsupported catalyst or on an inert support.

11. The process according to claim 1, wherein, after the hydrogenation, the xylylenediamine is purified by distilling off any solvent used and ammonia, and also any relatively low-boiling by-products, via the top and distillatively removing relatively high-boiling impurities via the bottom.

12. The process according claim 1, wherein, after the hydrogenation, any solvent used and ammonia and also any low-boiling by-products, are distilled off and, afterwards, xylylenediamine is removed from high-boiling impurities by distillation.

13. The process according to claim 11, wherein the xylylenediamine, after the distillation, is extracted for further purification with an organic solvent.

14. The process according to claim 13, wherein cyclohexane or methylcyclohexane are used for the extraction.

15. The process according to claim 2, wherein, after the removal of the high boilers, the NMP is removed partly or completely and/or low boilers are removed distillatively via the top.

16. The process according to claim 2, wherein the phthalonitrile for the hydrogenation step is dissolved or suspended in NMP, xylene, benzylamine, tolylamine and/or xylylenediamine.

17. The process according to claim 3, wherein the phthalonitrile for the hydrogenation step is dissolved or suspended in NMP, xylene, benzylamine, tolylamine and/or xylylenediamine.

18. The process according to claim 4, wherein the phthalonitrile for the hydrogenation step is dissolved or suspended in NMP, xylene, benzylamine, tolylamine and/or xylylenediamine.

19. The process according to claim 5, wherein the phthalonitrile for the hydrogenation step is dissolved or suspended in NMP, xylene, benzylamine, tolylamine and/or xylylenediamine.

* * * * *